(12) United States Patent
Najafi et al.

(10) Patent No.: US 8,206,325 B1
(45) Date of Patent: Jun. 26, 2012

(54) AMBULATORY SYSTEM FOR MEASURING AND MONITORING PHYSICAL ACTIVITY AND RISK OF FALLING AND FOR AUTOMATIC FALL DETECTION

(75) Inventors: Bijan Najafi, Highland Park, IL (US); Ashkan Vaziri, Brookline, MA (US); Ali-Reza Boloori, Ann Arbor, MI (US)

(73) Assignee: Biosensics, L.L.C., Brookline, MA (US)

( * ) Notice: Subject to any disclaimer, the term of this patent is extended or adjusted under 35 U.S.C. 154(b) by 562 days.

(21) Appl. No.: 12/249,948

(22) Filed: Oct. 12, 2008

Related U.S. Application Data

(60) Provisional application No. 60/979,557, filed on Oct. 12, 2007.

(51) Int. Cl.
*A61B 5/103* (2006.01)
*A61B 5/117* (2006.01)
*G01P 15/00* (2006.01)
*G01C 9/00* (2006.01)
*G01C 17/00* (2006.01)
*G01C 19/00* (2006.01)

(52) U.S. Cl. ........ 600/595; 600/587; 702/141; 702/150; 702/152; 702/153

(58) Field of Classification Search .................. 600/587, 600/595; 702/141, 150, 152, 153
See application file for complete search history.

(56) References Cited

U.S. PATENT DOCUMENTS

| | | | |
|---|---|---|---|
| 6,119,516 A | 9/2000 | Hock | |
| 6,201,476 B1 | 3/2001 | Depeursinge et al. | |
| 6,433,690 B2 * | 8/2002 | Petelenz et al. | 340/573.1 |
| 6,997,882 B1 | 2/2006 | Parker et al. | |
| 7,141,026 B2 | 11/2006 | Aminian et al. | |
| 7,334,472 B2 | 2/2008 | Seo et al. | |

(Continued)

FOREIGN PATENT DOCUMENTS

EP  1195139 A1  4/2002

(Continued)

OTHER PUBLICATIONS

B. Najafi, K. Aminian, F. Loew, Y. Blanc, and P. A. Robert, "Measurement of standsit and sit-stand transitions using a miniature gyroscope and its application in fall risk evaluation in the elderly," Ieee Transactions on Biomedical Engineering, vol. 49, pp. 843-851, 2002.

(Continued)

*Primary Examiner* — Max Hindenburg
*Assistant Examiner* — Devin Henson
(74) *Attorney, Agent, or Firm* — Knobbe Martens Olson & Bear LLP

(57) ABSTRACT

The present invention relates to a light-weight, small and portable ambulatory sensor for measuring and monitoring a person's physical activity. Based on these measurements and computations, the invented system quantifies the subject's physical activity, quantifies the subject's gait, determines his or her risk of falling, and automatically detects falls. The invention combines the features of portability, high autonomy, and real-time computational capacity. High autonomy is achieved by using only accelerometers, which have low power consumption rates as compared with gyroscope-based systems. Accelerometer measurements, however, contain significant amounts of noise, which must be removed before further analysis. The invention therefore uses novel time-frequency filters to denoise the measurements, and in conjunction with biomechanical models of human movement, perform the requisite computations, which may also be done in real time.

22 Claims, 8 Drawing Sheets

U.S. PATENT DOCUMENTS

| | | | |
|---|---|---|---|
| 7,620,450 | B2 | 11/2009 | Kim et al. |
| 7,627,450 | B2 | 12/2009 | Lee et al. |
| 7,634,379 | B2 | 12/2009 | Noble |
| 7,640,134 | B2 | 12/2009 | Park et al. |
| 7,725,289 | B2 | 5/2010 | Nagashima et al. |
| 7,747,409 | B2 | 6/2010 | Ladetto et al. |
| 7,857,771 | B2 | 12/2010 | Alwan et al. |
| 7,962,308 | B2 | 6/2011 | Makino |
| 7,983,872 | B2 | 7/2011 | Makino et al. |
| 8,007,450 | B2 | 8/2011 | Williams |
| 2003/0065409 | A1 | 4/2003 | Raeth et al. |
| 2003/0139692 | A1* | 7/2003 | Barrey et al. ............ 600/595 |
| 2004/0015103 | A1* | 1/2004 | Aminian et al. ............ 600/595 |
| 2006/0270949 | A1* | 11/2006 | Mathie et al. ............ 600/595 |
| 2008/0281555 | A1 | 11/2008 | Godin et al. |
| 2009/0069724 | A1* | 3/2009 | Otto et al. ............ 600/595 |
| 2009/0192414 | A1 | 7/2009 | Yasuhara |
| 2010/0286571 | A1 | 11/2010 | Allum et al. |

FOREIGN PATENT DOCUMENTS

WO    WO 03/065891 A2    8/2003

OTHER PUBLICATIONS

B. Najafi, K. Aminian, A. Paraschiv-Ionescu, F. Loew, C. J. Bula, and P. Robert, "Ambulatory system for human motion analysis using a kinematic sensor: Monitoring of daily physical activity in the elderly," *Ieee Transactions on Biomedical Engineering*, vol. 50, pp. 711-723, 2003.

R. W. Bohannon, A. W. Andrews, and M. W. Thomas, "Walking speed: reference values and correlates for older adults," *J Orthop Sports Phys Ther*, vol. 24, pp. 86-90, 1996.

K. Aminian, B. Najafi, C. Bula, P. F. Leyvraz, and P. Robert, "Spatio-temporal parameters of gait measured by an ambulatory system using miniature gyroscopes," *Journal of Biomechanics*, vol. 35, pp. 689-699, 2002.

K. Aminian, K. Rezakhanlou, E. De Andres, C. Fritsch, P. F. Leyvraz, and P. Robert, "Temporal feature estimation during walking using miniature accelerometers: an analysis of gait improvement after hip arthroplasty," *Medical & Biological Engineering & Computing*, vol. 37, pp. 686-691, 1999.

S. R. Cummings, M. C. Nevitt, and S. Kidd, "Forgetting falls. The limited accuracy of recall of falls in the elderly," *J Am Geriatr Soc*, vol. 36, pp. 613-6, 1988.

D. Oliver, M. Britton, P. Seed, F. C. Martin, and A. H. Hopper, "Development and evaluation of evidence based risk assessment tool (STRATIFY) to predict which elderly inpatients will fall: case-control and cohort studies," *Bmj*, vol. 315, pp. 1049-1053, 1997.

M. E. Tinetti, T. F. Williams, and R. Mayewski, "Fall risk index for elderly patients based on number of chronic disabilities," *Am J Med*, vol. 80, pp. 429-434, 1986.

K. Doughty, R. Lewis, and A. McIntosh, "The design of a practical and reliable fall detector for community and institutional telecare," *J Telemed Telecare*, vol. 6 Suppl 1, pp. S150-4, 2000.

U. Lindemann, A. Hock, M. Stuber, W. Keck, and C. Becker, "Evaluation of a fall detector based on accelerometers: a pilot study," *Med Biol Eng Comput*, vol. 43, pp. 548-551, 2005.

N. Noury, G. Barralon, G. Virone, P. Boissy, M. Hamel, and P. Rumeau, "A smart sensor based on rules and its evaluation in daily routines," presented at 25th Annual International Conference of the IEEE Eng. Med. Biol. Society, 2003.

\* cited by examiner

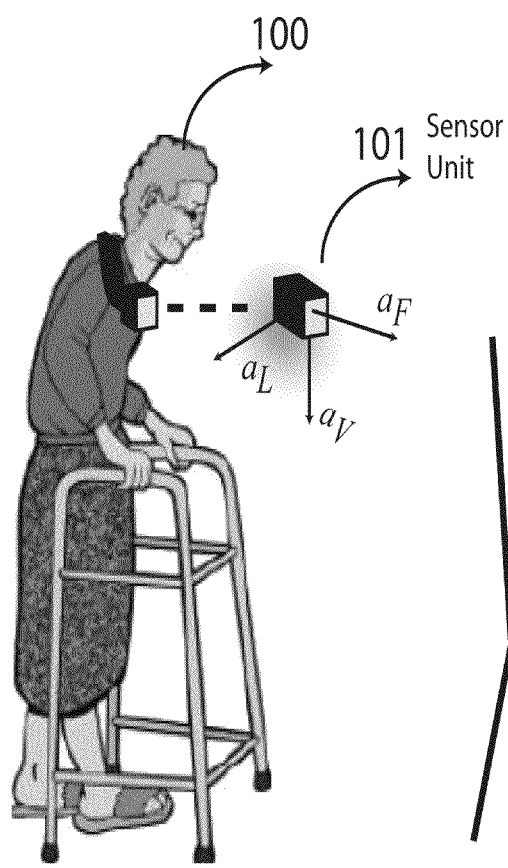
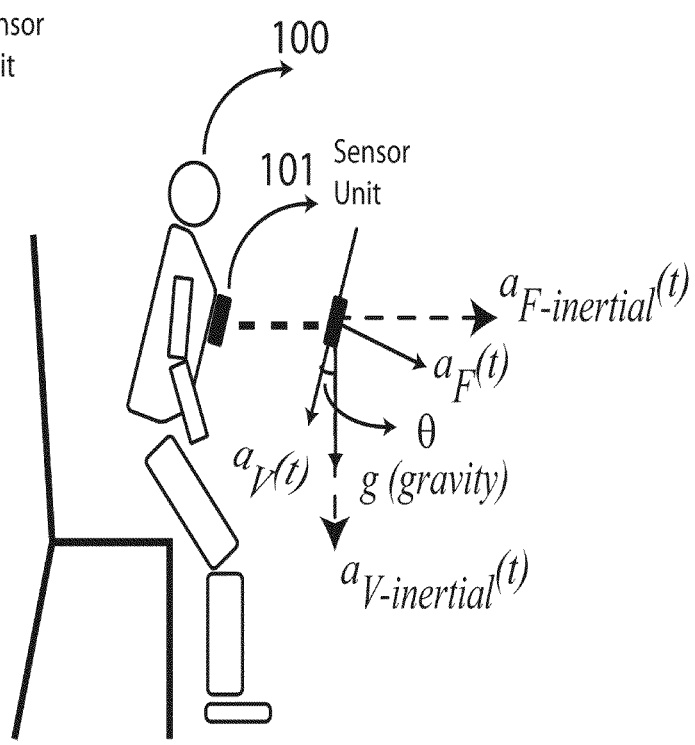
FIG. 1a
FIG. 1b

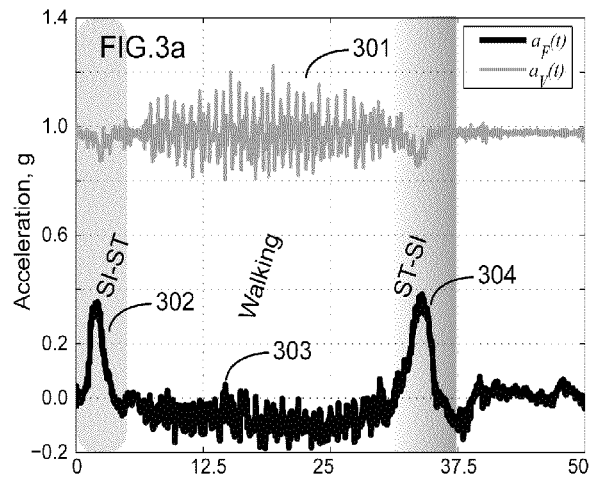
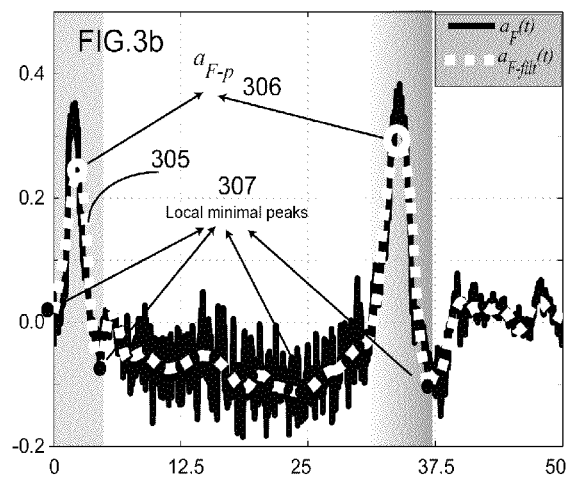
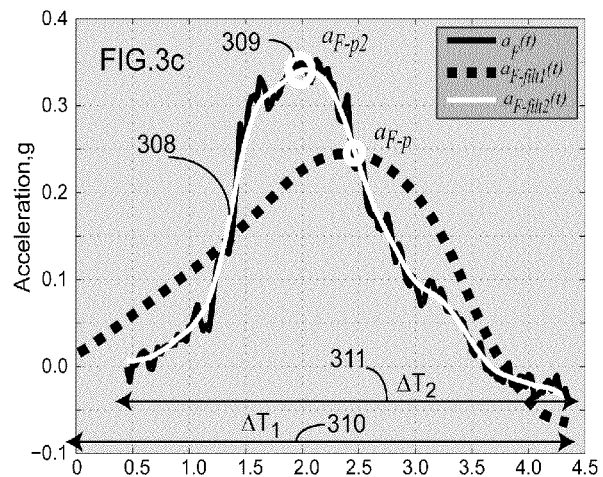
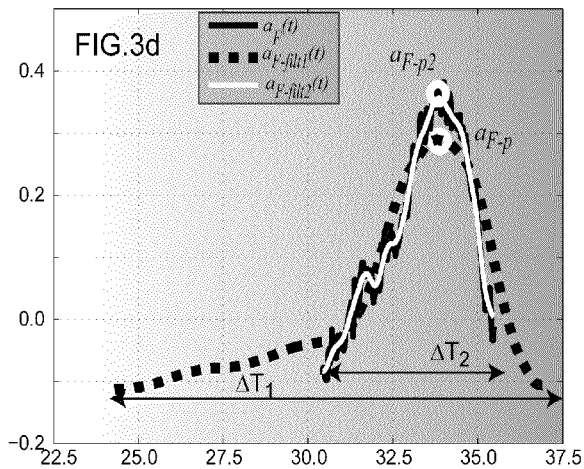
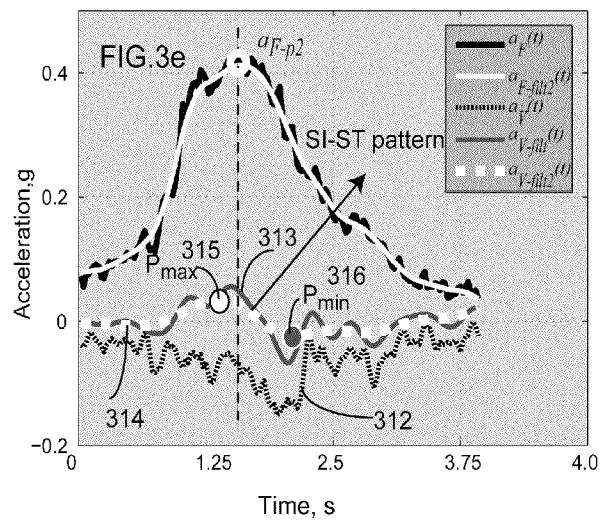
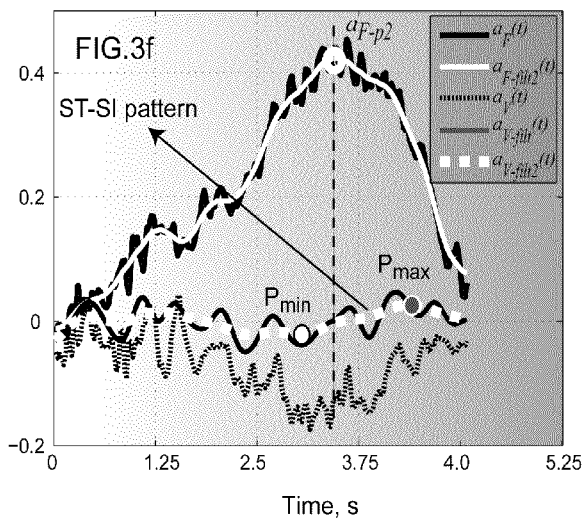

AMBULATORY SYSTEM FOR MEASURING AND MONITORING PHYSICAL ACTIVITY AND RISK OF FALLING AND FOR AUTOMATIC FALL DETECTION

CROSS-REFERENCE TO RELATED APPLICATIONS

This application claims the benefit of provisional patent application Ser. No. 60/979,557, filed 2007 Oct. 12 by inventors Bijan Najafi and Ashkan Vaziri.

FEDERALLY SPONSORED RESEARCH

Not Applicable

SEQUENCE LISTING OR PROGRAM

Not Applicable

FIELD

This invention generally relates to body movement monitoring systems, specifically to an ambulatory system which (1) measures and quantifies parameters related to the user's postures and movements; (2) evaluates the user's risk of falling; and (3) automatically detects the user's falls.

BACKGROUND OF THE INVENTION AND PRIOR ART

We envision several uses for the present invention. In the fields of elderly care and physical therapy, the present invention finds several important uses. We envision that the invented system can provide both qualitative and quantitative monitoring of an elderly person's physical activity (PA) during his or her everyday life. This information is useful for several reasons: first, PA monitoring can accurately determine the user's state of physical and mental health, identifying subacute changes in their health status. For example, this system can detect early deteriorations in the amount and quality of the subjects' PA due to various health conditions (e.g., congestive heart failure, development of infections, etc.) Second, PA monitoring provides valuable information about the sequence of the elderly person's movements during the time window surrounding their falls. This information significantly aids the development of alert systems to predict, and ideally, prevent fall occurrences. Third, assessment of the effects of new drugs and pain treatments are significantly advanced through monitoring of the subjects' physical activity during his or her everyday life. Fourth, monitoring of PA in the elderly population can, over time, provide insight into qualitative and quantitative changes in PA as a result of all adverse physical events, such as functional declines or hospitalizations. Persons at risk can therefore be identified, and novel preventive interventional methods may be tailored to their needs. The invented system also finds use in remote monitoring and telecare of people suffering from various diseases, such as Alzheimer's, as well as of those recovering and rehabilitating from diseases and medical procedures.

In clinical research and studies, the invented system provides valuable insight into the mechanisms and factors influencing physical activity and balance by quantifying the subject's PA and risk of falling (RoF) in all contexts, including everyday life.

In drug development, the invented system can be used to study the role of various drugs and treatment procedures on the physical activity and RoF of people during clinical studies.

In athletics training, this system provides valuable feedback on the user's body movements, and can be a valuable tool for both training and on-field performance measurement.

Measurement and monitoring of PA by the present invented system also finds use in weight management by providing intelligent feedback to the user about his or her daily energy expenditures.

A. Prior Art—Postural Transitions:

Najafi et al. [1-3] have developed algorithms for identifying postural transitions (PT), e.g., sit-to-stand (SI-ST) and stand-to-sit (ST-SI) from data recorded by a gyroscopic sensor attached to the subject's trunk. The high power-consumption rates of gyroscopes, however, severely limits the applicability of these algorithms for applications outside of the laboratory (which include everyday life applications), since such a system has an autonomy of only a few hours, therefore requiring frequent recharging or exchanges of the battery. Although the addition of more batteries would increase the device's autonomy, it will also increase its size and weight, thus hindering the subject's natural movements.

By contrast, the algorithms developed as part of the present invention use accelerometer data in place of gyroscope data, and therefore enable long-term, autonomous operability of the system.

B. Prior Art—Gait Analysis:

Proper gait function (i.e., quality of gait) requires the ability to maintain safe gait while navigating in complex and changing environments, and to conform one's gait to different task demands. Furthermore, a person's quality of gait is closely linked to his or her overall state of health. For example, walking speed correlates with the individual's ability to live independently, with the ability to perform various activities of daily life (such as safely crossing a traffic intersection), and with reductions in the risk of falling [4].

Since evaluation of a person's overall health and quality of life are greatly facilitated by knowledge of his or her gait function during everyday life, a system that can automatically extract gait-related parameters with minimal hindrance of the user's movements is highly useful. To date, however, fully satisfactory methods and systems have not been developed. Current techniques for computing a person's gait parameters are primarily based on the use of vertical accelerometer signals, together with a peak-detection algorithm to identify the walking step. Such techniques, however, possess several important shortcomings.

First, they cannot remove the rotational artifacts generated by the body segment to which the sensor has been attached. These noise artifacts stem from the gravitational component of the accelerometer signal. While they can be easily removed in the case of healthy young subjects, such artifacts pose a key challenge to accurate computation of gait parameters in the case of patients and the elderly—who tend to walk slowly and may use walking aids. Second, current algorithms cannot discriminate between acceleration peaks associated with postural transitions, and those due to walking steps, thus leading to very low specificity during activity daily life (ADL).

Alternative technologies for estimating the gait pattern use combinations of gyroscopes and/or accelerometers attached to the lower limbs [5-7]. Use of gyroscopes decreases the autonomy of the system due to high power consumption. Moreover, attaching the sensors on lower limbs hinders the user's movements, who must carry the system during ADL.

The present invention accurately identifies the user's walking periods during ADL, discriminates between left and right gait steps, and estimates the spatiotemporal parameters of gait (e.g., swing, stance, double support, and gait speed) using only accelerometers. Aminian et al. (1999) [7] have suggested an algorithm, based on a neural network, that extracts spatiotemporal parameters of gait using accelerometers attached to the subject's lower back. This algorithm, however, requires a calibration/pre-learning stage that can only be accomplished by having subjects walk within a constrained space of a gait lab. This requirement renders that algorithm impractical for use during everyday life activities. By contrast, the algorithms developed as part of the present invention require no initial calibrations, and therefore can be easily used by any individual.

In so doing, our algorithms overcome the shortcomings present in the prior art: the small, lightweight and portable sensory module, attached to the subject's chest, poses minimal hindrance to his or her movements during ADL. Furthermore, the accelerometers consume considerably less power than do gyroscopes, leading to significantly longer operational times. Moreover, the invented system provides significantly higher accuracy in discriminations, and better removes rotational noise artifacts.

C. Prior Art—Risk of Falling:

Evaluation of the individual's risk of falling is required in providing adapted assistance and preventive measures for subjects deemed at a high risk of falling. This risk is generally evaluated by using questionnaires, which have shortcomings such as subjectivity and limited accuracy in recall [8]. Risk of falling can also be evaluated by clinical and functional tests, such as assessments of posture and gait, independence in daily life, cognition, and vision [9-10]. However, an objective method for remotely monitoring this risk through the monitoring the daily physical activity (PA) has not yet been developed. By contrast, the present invention assesses and monitors the user's risk of falling through monitoring and measurement of his or her daily physical activity.

D. Prior Art—Automatic Fall Detection:

Of the health problems commonly associated with aging, the most serious is falling—defined as a person's trunk, knee, or hand unintentionally coming to rest on the ground or a lower level below the waist. A reliable system to remotely detect falls allows delivery of early care to these persons, and decreases the detrimental consequences of falls, leading to substantial health-care cost savings. Current fall alarm systems require activation and are therefore inappropriate in falls due to syncope, a loss of consciousness associated with cerebro-vascular accidents. Moreover, persons suffering from Alzheimer's disease—affecting approximately one-third of persons aged 80 years and older—may not be capable of activating such systems. A reliable system capable of sending automatic alarms when assistance is necessary will therefore provide an innovative way to support these patients and their caregivers. Automatic fall reporting would also be important in clinical research to reliably record occurrence of falls.

Current detection of falls essentially relies on self-reporting and complex reporting systems with daily phone-call reminders. In fact, for the research community interested in fall prevention, the documentation of falls is a methodological pitfall, and no unanimously accepted method for reporting falls exists. Little data support claims to the reliability and validity of different reporting systems. Oral reports have many limitations due to the cognitive status of the subjects as well as mental factors such as shame or fear of reporting. Finally, fall events associated with loss of consciousness due to syncope, stroke or epileptic seizures are not always recognized.

While a number of different approaches to fall detection have appeared in recent years [11-14], they have primarily used patterns recorded by tri-axial accelerometers to identify shocks related to falls, independent of the previous posture (i.e. sitting, lying, standing) and/or the state of activity (e.g. rest, walking, turning, postural transition, etc) of the faller. Not using the key information about the person's previous posture and state of activity likely gives rise to false detections, dramatically decreasing the accuracy of the fall detector. The present invention, by contrast, identifies falls with high sensitivity and specificity using only signals from accelerometers.

SUMMARY

The present invention consists of a body movement monitoring system that includes a sensing unit, attachable to the upper part of the user's body, such as trunk or shoulder, comprising a tri-axial accelerometer, or, three mono-axial accelerometers measuring accelerations in three perpendicular directions. The system also includes one or more processor circuits configured to: process the signals recorded by the accelerometer(s) and derive information related to the subject's movement from said accelerometer(s). Some or all of these analyses may be carried out on-board the sensing unit. In all cases, software-based algorithms, developed as part of the present invention, are integrated with the processor circuits performing the analyses. One or more data storage systems are also included in the system, and are configured to store signals recorded by said accelerometer(s), or the information derived by one of said processor circuits, or both. One or more of said data storage systems may be housed within said sensor. An optional communications system, configured to transmit at least a portion of the data recorded by said accelerometers, or at least a portion of the information derived by said the processor circuit housed within the sensor, or both, may also be housed with the sensor. The information derived from the measured acceleration signals are used to monitor and quantify the user's physical activity; automatically detect the user's risk of falling; and assess the user's risk of falling. The required computations are performed according to software-based algorithms, developed as part of the present invention, which use at least one biomechanical model of human body movement, and one or more signal processing time-frequency filters.

BRIEF DESCRIPTION OF THE DRAWINGS

The foregoing and other objects, features, and advantages of the invention will be apparent from the following detailed description of the invention, as illustrated in the accompanying drawings, in which like reference numerals designate like parts throughout the figures thereof and wherein:

FIG. 1a illustrates how an elderly subject may wear the sensory module, and also shows the three components of acceleration measured by the sensory unit;

FIG. 1b is a two-dimensional schematic of a subject wearing the sensory unit, and shows the subject's trunk lean angle θ, the direction of gravity, as well as the frontal and vertical acceleration components;

FIG. 3 demonstrates the operation of the algorithms in determining the time, type and duration of the subject's postural transitions;

DETAILED DESCRIPTION OF EXEMPLARY EMBODIMENTS

Figure 2:
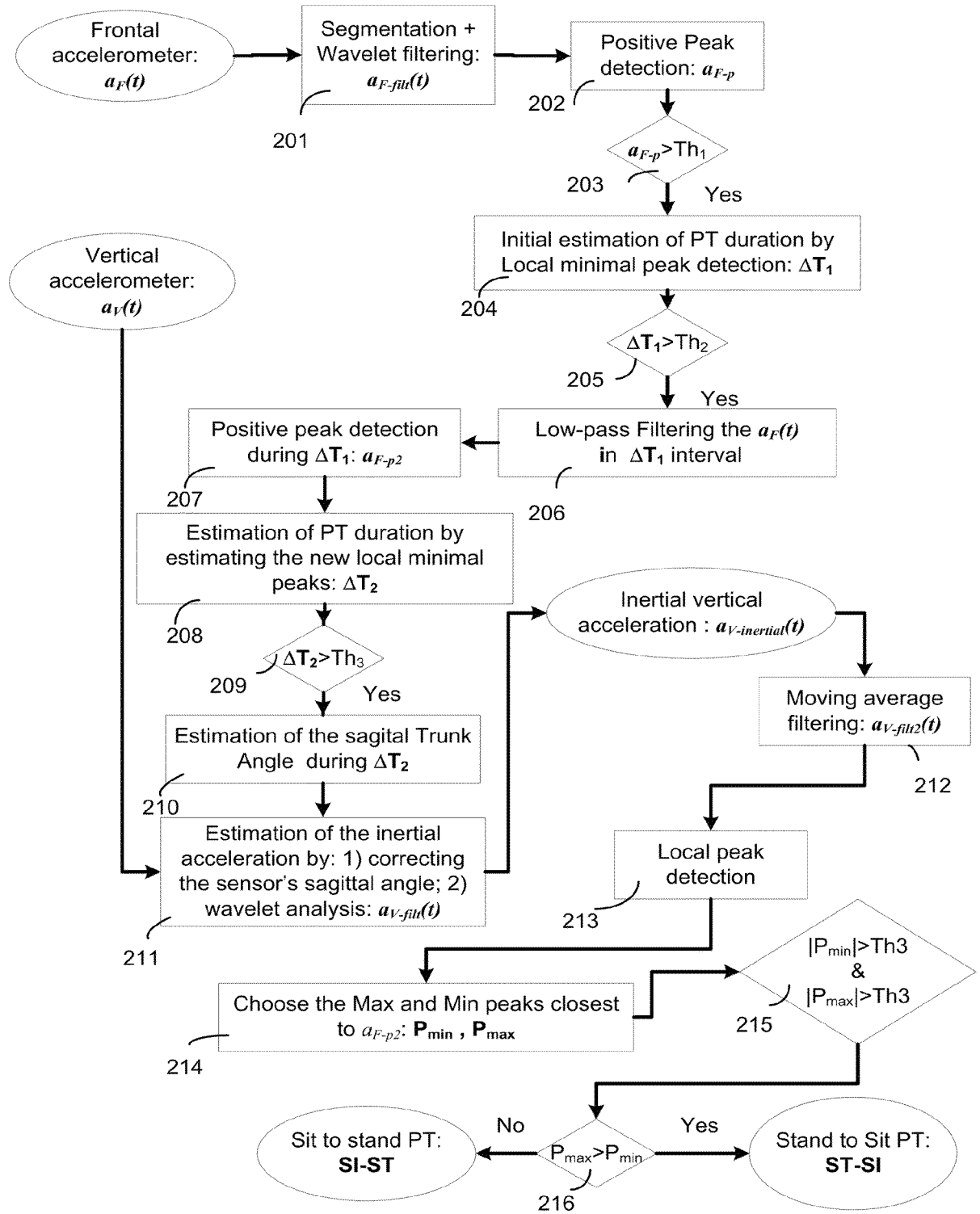
FIG. 2 is a flowchart of the algorithms used to determine the time, time and duration of the subject's postural transitions.

The present invention consists of a system and method for performing the following tasks during the user's everyday life: (1) monitoring the user's physical activity; (2) automatically detecting the user's falls; and (3) assessing the user's risk of falling. The second and third tasks are based on the results obtained from the first.

As shown by FIG. 1a, the system includes a sensing module ("SM") 101 for sensing, filtering and analyzing the user's 100 body movements. The SM 101 is positioned on the user's 100 upper body (typically, on the user's chest or torso), and is comprised of one to three accelerometers, each of which may be mono-axial or multi-axial. The only constraints on the accelerometer configuration are that (1) accelerations in three perpendicular directions must be measured; and (2) the accelerometer(s) is(are) configured to record accelerations in the frontal (F), vertical (V) and lateral (L) directions, which directions are relative to the user 100 (see FIG. 1a). In this document, all acceleration quantities are expressed in units of g (i.e., as multiples or fractions of g), where g is the gravitational constant equaling 9.81 m/s$^2$: for example, by this convention an acceleration magnitude of 9.81 m/s$^2$ (in SI units) will be expressed 1.

The SM 101 may also include a data-storage system for storing the measured accelerations. An optional on-board communications system provides the SM 101 the capability to transmit the collected data and/or analyzed signals through either wired or wireless links for storage and/or for further offline analysis.

Analysis of the measured acceleration signals may be carried out (1) entirely on-board the SM 101, (2) partially on-board the SM 101 and partially at other location(s), or (3) entirely at other location(s). In case some or all of the analysis is (are) carried out on-board the SM 101, a data processing circuit will be included on-board the SM to carry out the required computations according to software-based algorithms developed as part of the present invention. In case some or all of the analysis is carried at location(s) separate from the SM 101, the required data processing circuits performing the analysis may be ordinary or special-purpose computers, and are integrated with software-based algorithms developed as part of the present invention.

A. Monitoring the User's Physical Activity

Monitoring the user's physical activity consists of monitoring and assessing the user's postures, movements, trunk tilt, as well as fall-related task parameters. To this end, the system computes various parameters associated with the subject's movement from the data recorded by the SM 101. These parameters consist of: (a) the subject's trunk tilt (specified in degree, measuring the angle between the subject's trunk axis, and the axis aligned with the gravitational force—see FIG. 1b); (b) the type of the subject's postural transitions (PT); (c) the time of the subject's postural transitions; (d) the duration of the subject's postural transitions; (e) the duration of the subject's locomotion; (f) characterization of the subject's locomotion (gait analysis); and (g) the type of subject's postures (e.g., sitting, standing, lying).

Use of accelerometers in place of gyroscopes by the present invention allows for long-term autonomous operability of the system. The associated challenges introduced by this replacement, however, consist of processing the resulting noisy accelerometer signals during everyday living activities.

I. Identifying the Types of Postural Transitions, and Computing their Durations and Occurrences:

The flowchart in FIG. 2 and FIGS. 3a-3f demonstrate the operation of the algorithms, developed as part of the present invention, used to continuously determine the type, time, and duration of the subject's postural transitions (in this case, SI-ST and ST-SI) during everyday movements. The algorithms use the frontal and vertical accelerometer signals—$a_F(t)$ and $a_V(t)$ respectively in FIG. 1a—where their time-varying nature is explicitly shown by including the time variable t in the notation used for these signals. In implementing the algorithms, the time variable t is by necessity discrete.

FIG. 3a shows an example of the acceleration patterns recorded by the vertical and frontal accelerometers from an elderly subject with a high risk of falling ($a_V(t)$: gray line 301; $a_F(t)$: black line). As identified on the plot, the pattern consists of a sit-to-stand (SI-ST) postural transition followed by a period of walking and turning, followed by another postural transition (stand-to-sit; ST-SI).

As shown in FIG. 2, the algorithm performs the following steps on the frontal accelerometer signal to determine the occurrence, duration and type of the postural transitions:

1) segmenting, followed by wavelet filtering (box 201 in FIG. 2) to remove signal artifacts induced by locomotion (e.g., walking, climbing or descending the stairs, etc.)—see also the white trace 305 in FIG. 3b, an example of the resulting filtered signal $a_{F\text{-}filt}(t)$;

2) locating the local maximum peaks (denoted by $a_{F\text{-}p}$ 306 in FIG. 3b) in the filtered signal $a_{F\text{-}filt}(t)$ 305 through a peak-detection algorithm—this step corresponds to box 202 in FIG. 2;

3) for each postural transition, corresponding to a particular $a_{F\text{-}p}$ 306, computing an initial estimate of the postural transition duration ($\Delta T_1$) by (boxes 203 and 204):

(i) determining whether $a_{F\text{-}p}$ 306 is greater than a pre-defined threshold Th1;

(ii) if yes, locating the local minima 307 in $a_{F\text{-}filt}(t)$ 305, within a specified time window, that precede and follow the particular maximum peak $a_{F\text{-}p}$ 306—see FIG. 3b;

(iii) computing $\Delta T_1$ 310 as the duration of the resulting time interval $I_1$ separating the local minima computed above.

The above steps suppress and remove signal artifacts, such as noisy peaks, associated with shocks or other locomotion activities.

Following the initial determination of the postural transition duration ($\Delta T_1$), the system computes a more accurate estimate of the postural transition duration, $\Delta T_2$, by applying additional filters to the frontal acceleration signal only within a time interval that is centered at $I_1$, but that is typically 10% to 30% longer in duration than $\Delta T_1$ 310. Such filtering of the frontal acceleration signal significantly decreases the requisite calculation costs, therefore enabling real-time implementation of the algorithm.

If the value $\Delta T_1$ 310 surpasses a defined threshold, $Th_2$ (box 205 in FIG. 2), the following steps are performed on the frontal accelerometer signal $a_F(t)$ only during a time interval that is centered at $I_1$ but that is typically 10% to 30% longer in duration:

1) as represented by box 206 in FIG. 2, low-pass filtering the $a_F(t)$ signal during the time interval $I_1$ by a wavelet;
2) as represented by box 207 in FIG. 2, locating the maximum peak ($a_{F-p2}$ 309) in the resulting filtered signal $a_{F-filt2}(t)$ 308 during time interval $I_1$ (see FIG. 3c);
3) within a specified time window, locating a local minimum in $a_{F-filt2}(t)$ closest to, and preceding, the particular maximum peak $a_{F-p2}$ (box 207 in FIG. 2);
4) within a specified time window, locating a local minimum in $a_{F-filt2}(t)$ closest to, and following the same maximum peak (box 207 in FIG. 2);
5) computing $\Delta T_2$ 311 (see FIG. 3c) as the duration of the resulting time interval $I_2$ separating the local minima computed above (box 207 in FIG. 2);

The time of the maximum peak $a_{F-p2}$ represents the time of the postural transition, and the parameter $\Delta T_2$ 311 represents the estimate of the duration of the postural transition.

For each postural transition, following the computation of its time of occurrence and its duration, the system uses the step-by-step algorithm below to identify its type (e.g., ST-SI or ST-SI):

1) as represented by boxes 209 and 210 in FIG. 2, for each postural transition if $\Delta T_2$ exceeds a predefined threshold $Th_3$, estimate the trunk tilt angle in the sagittal plane, $\theta$, using a low-pass filtering of the $a_F(t)$ signal during the corresponding time interval $I_2$—since $a_F(t)$ consists of a $\theta$-dependent gravitational component as well as a higher-frequency, pure frontal-acceleration component, low-pass filtering removes the pure frontal-acceleration component, leading to a quantity proportional to the $\sin(\theta)$;
2) estimate the time-varying inertial frontal and vertical accelerations $a_{F-interial}(t)$ and $a_{V-interial}(t)$ through the following coordinate transformation (see box 211 in FIG. 2):

$$\begin{bmatrix} a_{F-inertial}(t) \\ a_{V-inertial}(t) \end{bmatrix} = \begin{bmatrix} \cos(\theta(t)) & -\sin(\theta(t)) \\ \sin(\theta(t)) & \cos(\theta(t)) \end{bmatrix} \begin{bmatrix} a_F(t) \\ a_V(t) \end{bmatrix} + \begin{bmatrix} 0 \\ 1 \end{bmatrix},$$

where, as mentioned before, the acceleration signal is expressed in units of g (g represents the gravitational constant (9.81 m/s$^2$))—see also FIG. 1b for a free-body diagram showing the inertial acceleration components;
3) in parallel, apply an adequate, cascaded low-pass filter to remove the artifacts from $a_V(t)$, where the low-pass filter functions as follows:
   (i) removal of the gravitational component of $a_V(t)$ 312 (FIG. 3e) using the following equations (see also box 211 in FIG. 2):

$$a_F(t) = [a_{V-inertial}(t)+1]\sin(\theta(t)) + a_{F-inertial}(t)\cos(\theta(t));$$

$$a_V(t) = [a_{V-inertial}(t)+1]\cos(\theta(t)) - a_{F-inertial}(t)\sin(\theta(t));$$

$$a_{V-filt}(t) = \sqrt{[a_F(t)]^2 + [a_V(t)]^2};$$

(ii) low-pass filtering the resulting signal $a_{V-filt}(t)$ 313, leading to $a_{V-filt2}(t)$; and
   (iii) filtering this signal by a moving-average filter to obtain $a_{V-filt3}(t)$ (see also box 212 in FIG. 2);
4) as exemplified in FIGS. 3e-3f, determine the local peaks in $a_{V-filt}(t)$ using a peak-detection algorithm (box 213 in FIG. 2); the resulting positive and negative peaks—$P_{max}$ 315 and $P_{min}$ 316, respectively—exceeding a predefined threshold $Th_4$, are identified (boxes 214 and 215 in FIG. 2);
5) classify the detected postural transition as sit-to-stand or stand-to-sit through the sequence by which $P_{max}$ and $P_{min}$ occur: e.g., a $P_{max}$ followed by a $P_{min}$ identifies the postural transition as a sit-to-stand pattern (box 316 in FIG. 2; see also FIGS. 3e-3f);
6) apply a post-processing algorithm to prevent misclassification of postures and postural transitions: for each postural transition, the classification as ST-SI or SI-ST will be corrected based on the preceding and subsequent sequences of postural transitions.

Figure 4:
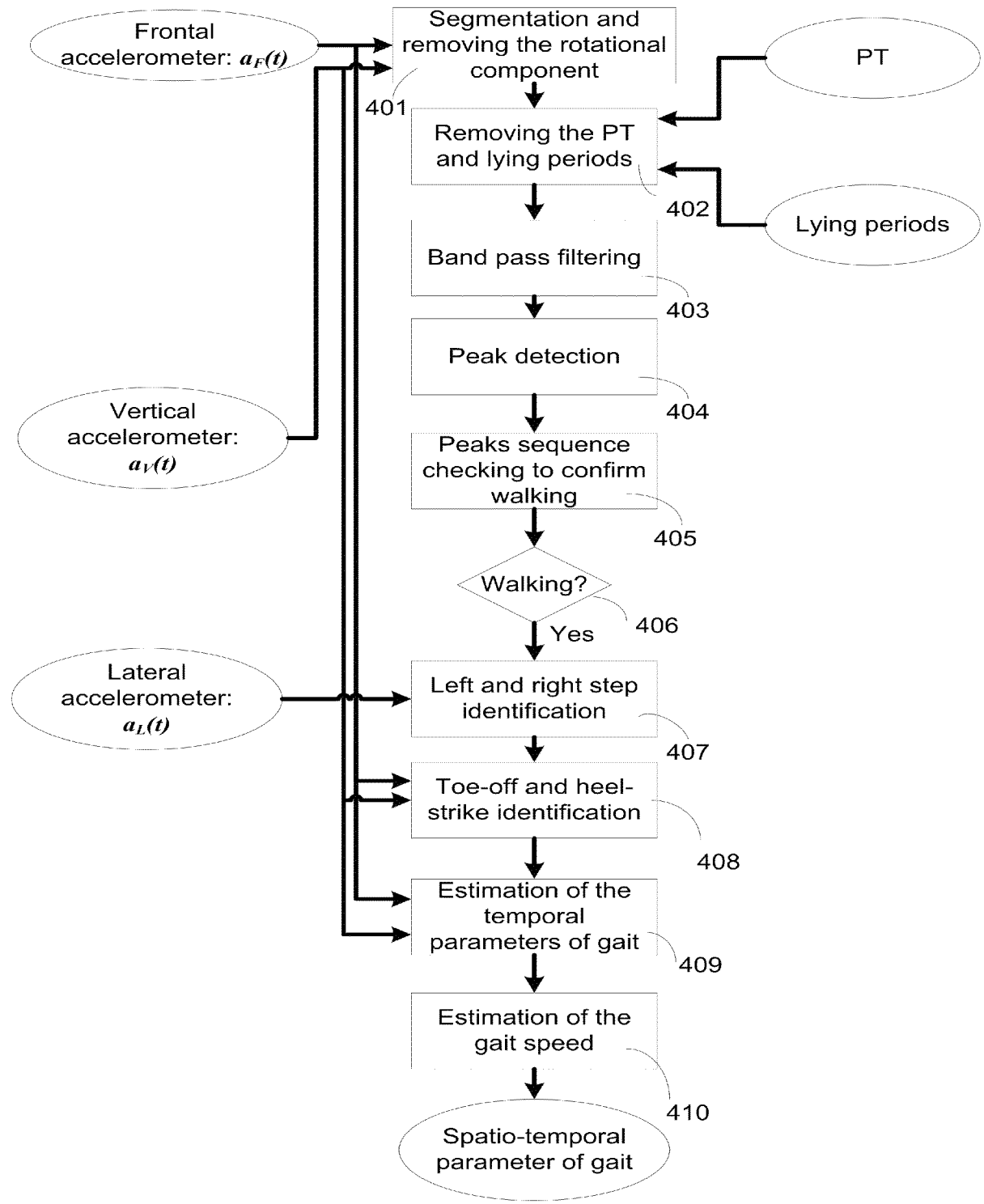
FIG. 4 is a flowchart of the algorithms used to identify the walking periods, and to compute the subject's spatiotemporal parameters of gait.

II. Analyzing Gait, and Identifying the Corresponding Walking Periods:

FIG. 4 describes in flowchart form the software-based algorithm, developed as part of the invented system, to identify the subject's walking periods and measure his or her gait parameters. Using data recorded by the accelerometers, the algorithm can distinguish left and right gait steps, as well estimate the spatiotemporal gait parameters, e.g., swing, stance, double support, and gait speed.

Figure 5:
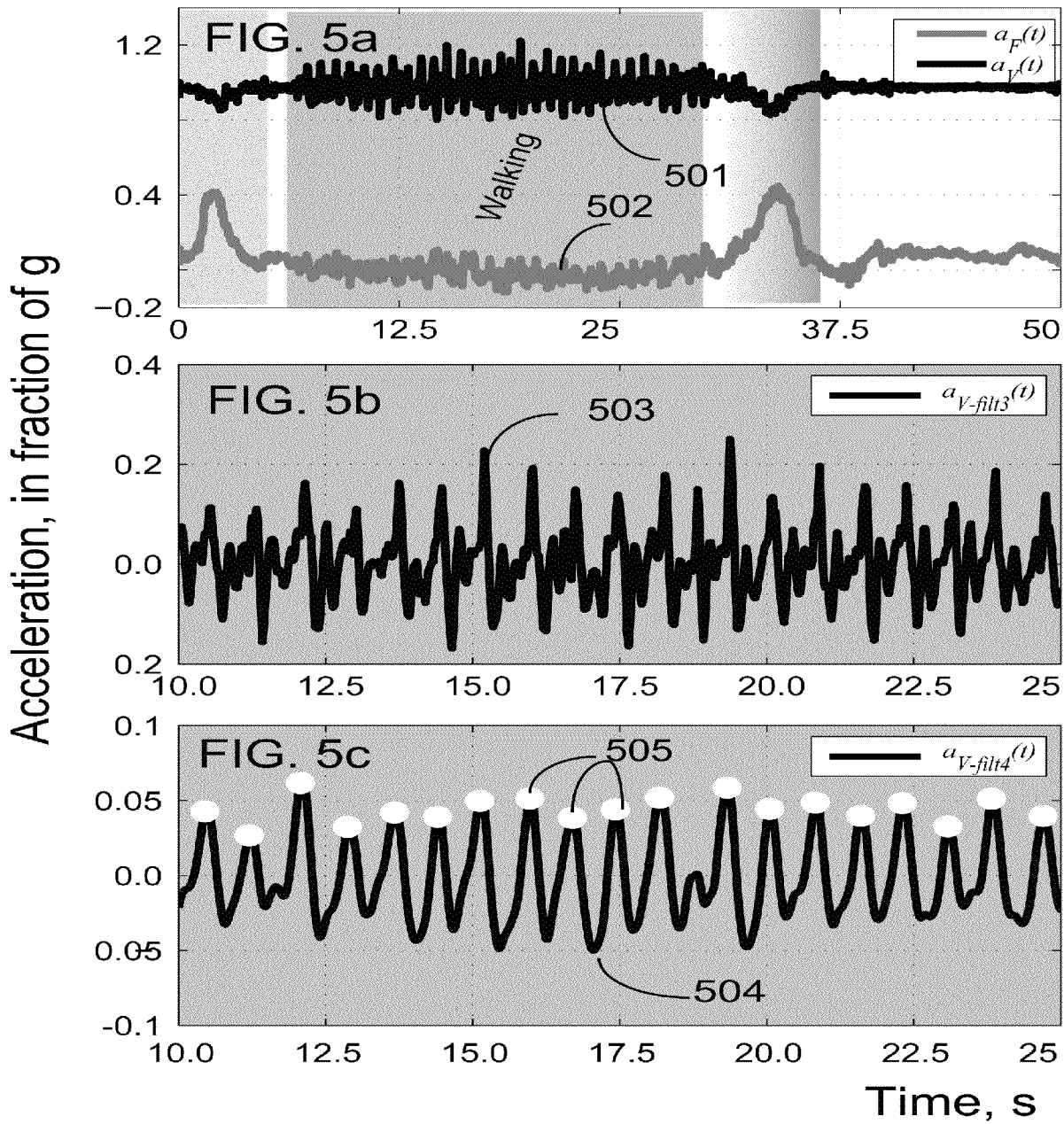
FIG. 5 demonstrates the operation of the algorithms in identifying the walking periods, and in computing the subject's spatio-temporal parameters of gait.

The algorithm consists of the following steps:

1) remove from consideration data during time periods associated with postural transitions and lying (boxes 401-402 in FIG. 4);
2) compute the time-varying norm (i.e., time-varying magnitude) of the vertical and horizontal accelerometer signals as:

$$a_F(t) = [a_{V-inertial}(t)+1]\sin(\theta(t)) + a_{F-inertial}(t)\cos(\theta(t));$$

$$a_V(t) = [a_{V-inertial}(t)+1]\cos(\theta(t)) - a_{F-inertial}(t)\sin(\theta(t));\text{ and}$$

$$a_{V-filt3}(t) = \sqrt{[a_F(t)]^2 + [a_V(t)]^2};$$

where $\theta(t)$ represents the time-varying trunk angle, and $a_{V-inertial}(t)$ and $a_{F-inertial}(t)$ represent the time-varying vertical and frontal acceleration components, respectively; FIG. 5b shows the resulting waveform, $a_{V-filt3}(t)$ 503—see FIG. 1b for the free-body diagram leading to the above formulas; these formulas allow for suppression of the movement artifacts derived from the rotations of the subject's trunk;
3) remove the gravitational component from the vertical acceleration signal in two steps: first, use formula stated in step (2) to compute $a_{V-filt}(t)$ 503; second, as shown by box 403 in FIG. 4, band-pass filter the result, leading to $a_{V-filt}(t)$ 504 (see FIG. 5c);
4) as represented by box 404 in FIG. 4, identify gait steps as the peaks 505 (see, FIG. 5c) in the $a_{V-filt4}(t)$ signal 504;
5) verify the sequence of the detected peaks according to pre-defined conditions for gait patterns (box 405 in FIG. 4);

6) distinguish left and right steps (box 407 in FIG. 4) using the signal $a_L(t)$ from the lateral accelerometer—specifically, (i) the subject's lateral velocity $v_L(t)$ is computed by integrating $a_L(t)$ during the recognized walking periods; (ii) the relationship between the locations of the positive and negative peaks in $v_L(t)$ with the identified peak in the filtered vertical acceleration signal, $a_{V\text{-}filt4}(t)$ 504, allows for left and right steps be distinguished.

This algorithm, furthermore, enables both the recognition of undetected gait steps, and the removal of false detected steps.

The system, through another algorithm, computes the times of heel-strike (initial contact) and toe-off (final contact) events using information extracted from the frontal and vertical acceleration signals—this step corresponds to box 408 in FIG. 4. Specifically, the local minimum and maximum peaks in the frontal acceleration signal surrounding each identified vertical acceleration peak are used to identify heel-strike event and toe-off events. Following a heel-strike event, the subject's trunk continues to moves forward. As the toe-off event occurs, the trunk slows down, leading to a negative peak in the frontal accelerometer signal. Although a heel-strike event can be estimated using the vertical acceleration signal, when an impact is identified, the positive peak of the frontal acceleration pattern offers a significantly lesser noisy source for identification of the heel-strike event. Determination of these event times facilitates the measurement of the temporal parameters (e.g., stance, swing, double support, step time, gait cycle time, etc.) and other relevant information associated with the spatial parameters (i.e. stride velocity, step length and stride length).

Gait speed (i.e., stride velocity) is computed (box 410 in FIG. 4) using information from the detected gait cycle and the amplitude of acceleration during the double support.

III. Detecting and Classifying the Lying Posture.

The system distinguishes lying from sitting and standing by comparing the angle of the vertical accelerometer signal $a_V(t)$ to that of the gravitational component. While the vertical accelerometer measures almost zero during lying periods, its value is significantly greater during sitting and upright postures—in some cases the value is close to the gravitational constant.

Figure 6:
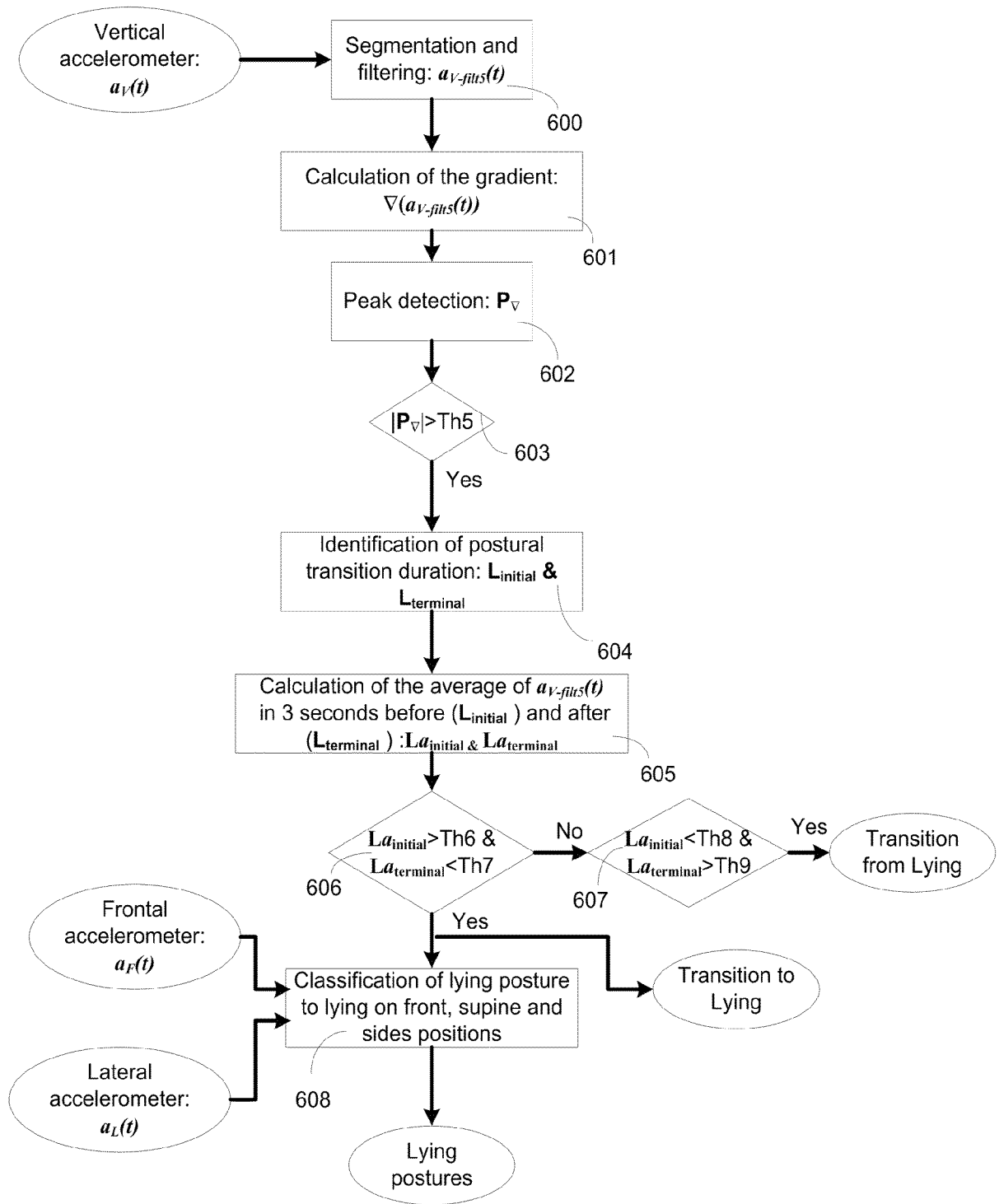
FIG. 6 is a flowchart of the algorithms used to detect and classify the lying posture.

The system identifies both the sit/stand-to-lying (SI/ST-L) and the mirror opposite (i.e., L-SI/ST) postural transitions using the following algorithm:

1) band-pass filter the vertical accelerometer signal (box 600 in FIG. 6);
2) calculate the gradient of the resulting the filtered signal $a_{V\text{-}filt5}(t)$ (box 601 in FIG. 6);
3) determine the maximum or minimum peak ($P_\nabla$) of this gradient (box FIG. 6, box 602);
4) if the absolute value of the detected peak $P_\nabla$ exceeds a pre-defined threshold $Th_5$ (box 603, FIG. 6), estimate the duration of lying postural transition using a local peak detection scheme to identify peaks preceding ($L_{initial}$) and following ($L_{terminal}$) $P_\nabla$ (box 604, FIG. 6);
5) identify a lying posture at the time of the detected peak when (i) the absolute value of the detected peak exceeds a threshold $Th_5$ (box 603, FIG. 6); and (ii) the average value of $a_{V\text{-}filt5}(t)$ during the 3 seconds preceding the $L_{initial}$ is higher than a pre-defined threshold $Th_6$ (boxes 605-606, FIG. 6); and (iii) the average value of $a_{V\text{-}filt5}(t)$ during the 3 seconds following the $L_{terminal}$ is lower than a threshold $Th_7$ (boxes 605-606, FIG. 6);
6) detect/identify a lying-to-sit/stand (L-SI/ST) postural transition at the time of the detected peak $P_\nabla$ when (i) the absolute value of the detected peak exceeds a pre-defined $Th_5$ (box 603, FIG. 6); and (ii) the average value of $a_{V\text{-}filt5}(t)$ during the 3 seconds preceding the $L_{initial}$ is lower than $Th_8$ (boxes 605-607, FIG. 6); and (iii) the average value of $a_{V\text{-}filt5}(t)$ during the 3 seconds following the $L_{terminal}$ is higher than a threshold $Th_9$ (boxes 605-607, FIG. 6);
7) classify the lying posture further as lying on back, lying on the front, or on the sides (left or right) on the basis of the value of the frontal accelerometer signal (box 608, FIG. 6);
8) further classify lying on the side into lying on the right and lying on the left according to the value of the lateral accelerometer signal.

Figure 7:
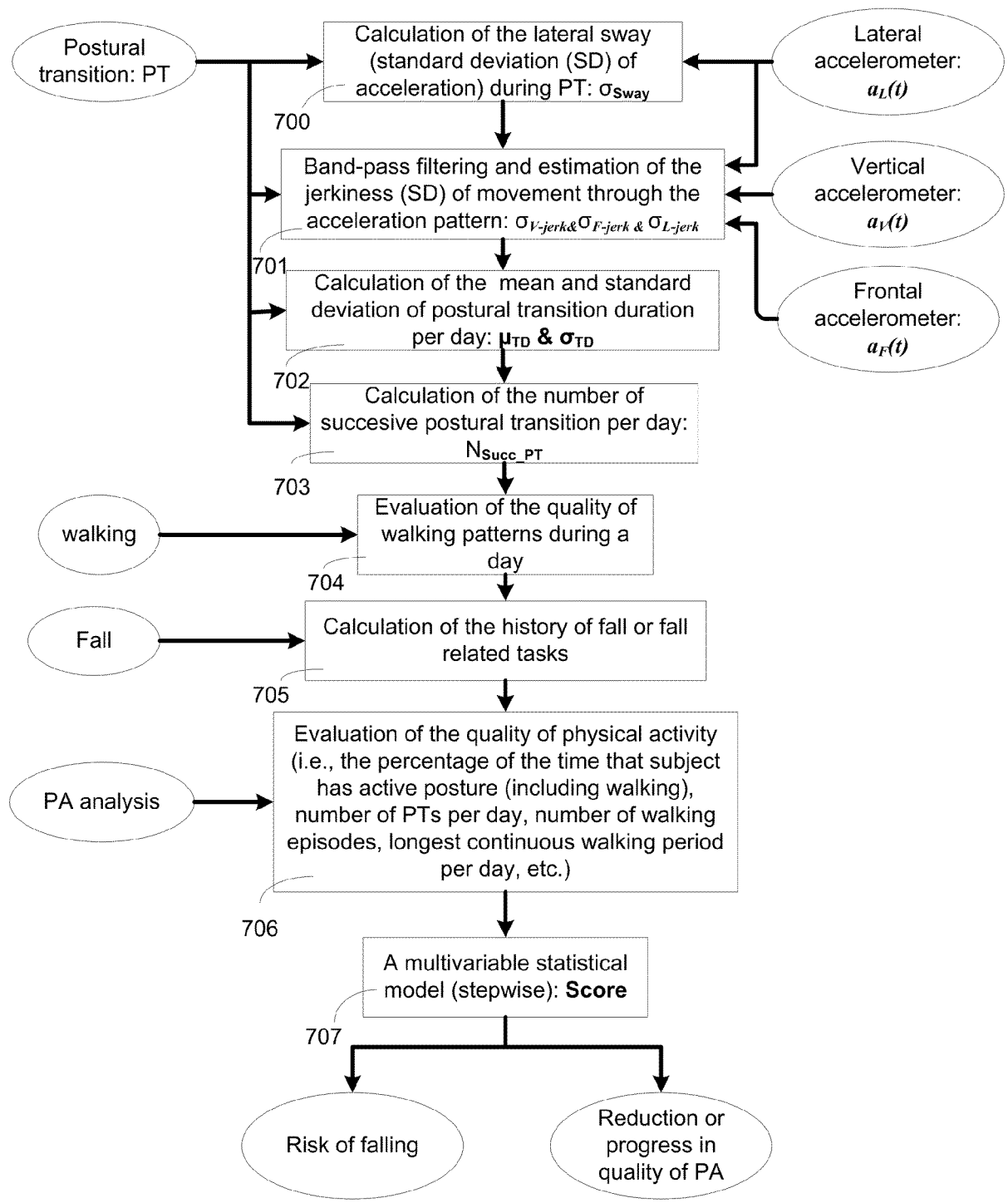
FIG. 7 is a flowchart of the algorithm used to compute the subject's risk of falling, and the quality of the subject's physical activity.

B. Computing the Risk of Falling and the Quality of the Subject's Physical Activity By monitoring the subject's physical activity, the invented system both evaluates the quality of the subject's physical activity, and computes the decline or progress in the subject's functional performance. FIG. 7 presents the flowchart of the corresponding software-based algorithm, developed as part of the invented system.

The subject's risk of falling (RoF) during everyday life is computed by first quantifying the quality of the subject's postural transitions. In turn, the quality of the postural transitions is quantified using the following algorithm:

1) estimate the lateral sway ($\sigma_{sway}$) of the subject during PT by computing the standard deviation of the lateral accelerometer during PT (box 700, FIG. 7);
2) estimate the jerkiness in the subject's movement in all directions ($\sigma_{V\text{-}jerk}$, $\sigma_{F\text{-}jerk}$, and $\sigma_{L\text{-}jerk}$)—computed as the standard deviation of the band-pass filtered acceleration signals in the frontal, vertical and lateral directions (box 701, FIG. 7);
3) compute the mean ($\mu_{TD}$) and standard deviation ($\sigma_{TD}$) of the durations of the subject's postural transitions ($\Delta T_2$), over a day (box 702, FIG. 7);
4) compute the number of successive postural transitions ($N_{Succ\_PT}$) required for a subject to accomplish a single task—an example is multiple unsuccessful attempts by a subject to rise from a chair (box 703, FIG. 7);
5) evaluate the quality of physical activity by computing the fraction of the time that subject has active posture (including walking); the number of PTs per day; the number of walking episodes during a day; and the longest continuous walking period per day (boxes 704-706, FIG. 7);
6) evaluate the subject's risk of falling by inputting the above parameters to a statistical model (e.g., stepwise) that provides a linear combination of the calculated parameters to yield a single score representative the subject's RoF (box 707, FIG. 7). A subject is considered to be at a high-risk of falling if the linear combination passes beyond a threshold, which may be predefined, or may change adaptively.

To identify a subject at a high risk of falling more accurately, the system continually adjusts the requisite threshold values based on the history of falls or other similar events detected by the algorithm (e.g., high-impact experienced shortly after a postural transition, very short ST-SI durations, etc.)

I. Automatic Fall Detection.

The present invention uses a novel algorithm, based solely on accelerometer signals, to automatically identify falls during the subject's everyday life with high sensitivity and specificity. The fall-detection algorithm described here uses information about the subject's physical activity, as well as posture. The flowchart in FIG. 8 describes in complete the algorithm developed to automatically detect the subject's falls. The following summarizes the algorithm:

1) compute the norm (magnitude) of acceleration in the transversal plane, $a_{trans}(t)$ from the frontal and lateral acceleration signals—$a_F(t)$ and $a_L(t)$, respectively—through: $a_{trans}(t) = \sqrt{[a_F(t)]^2 + [a_L(t)]^2}$ (box 800);
2) apply a peak-detection algorithm (box 801) to $a_{trans}(t)$ to identify the presence of "shocks" $a_{trans\text{-}Pmax}$;
3) confirm a fall event by considering the subject's PA and posture prior to impact times (marked by the identified shocks)—this step is carried out using algorithms described above;
4) use different algorithms to identify a fall event, depending on the results of step (3) supra:
   (i) if impacts occur while subject is walking or turning, depending on whether the impacts occurred after right or left step, the algorithm chooses appropriate thresholds and coefficients required for subsequent steps ($Th_8$: box 812; $Th_9$: box 814; and coefficients of the multivariable model: box 816);
   (ii) if activity preceding the shock is not identified as walking, turning or any sequential locomotion (e.g., walking upstairs or downstairs,) the algorithm would identify as fall events only the shocks that occur after a postural transition to sitting or lying.
   (iii) Next, thresholds and coefficients required for subsequent steps are modified;
5) segment the shock-pattern following a postural transition into pre-shock, impact, and post-shock phases based on the location of local minimum peaks relative to the absolute maximum peak ($p_{max}$) in the signal $a_{trans}(t)$ (box 810, FIG. 8); the set of thresholds chosen according to step (4) supra, and used by the algorithm depends on whether the post-shock posture is sitting or lying.
6) estimate the shock width $\Delta_{shock}$) using the local minimum peaks before and after each the peak $p_{max}$(box 811, FIG. 8); consider the peak to be an artifact and subsequently ignored if its width does not exceed the threshold $Th_8$ (box 812, FIG. 8);
7) if the peak is not an artifact, compute the subject's speed during the pre-shock phase by integrating the pattern of vertical accelerometer—$V_V(t)$ (box 813, FIG. 8); for the peak to be recognized as a fall, the peak of the velocity profile must exceed the threshold $Th_9$ (box 814, FIG. 8);
8) compute the following descriptors (box 815, FIG. 8):
   (i) sum of all accelerations at the time of impact $t_{impact}$ as:

$a_{total}(t_{impact}) = a_F(t_{impact}) + a_V(t_{impact}) + a_V(t_{impact})$;

(ii) the sum frontal and lateral accelerations at impact time:

$a_{F+L}(t_{impact}) = a_F(t_{impact}) + a_L(t_{impact})$;

(iii) the difference of speed in each direction at the impact time ($V_{F\text{-}impact}$, $V_{V\text{-}impact}$, and $V_{L\text{-}impact}$); and
   (iv) (iv) energy of the norm of vertical and frontal acceleration during the impact phase ($\Delta_{Shock}$):

$$E_{Impact} = \int_{\Delta_{Shock}} \sqrt{a_F(t)^2 + a_V(t)^2}\, dt;$$

Figure 8:
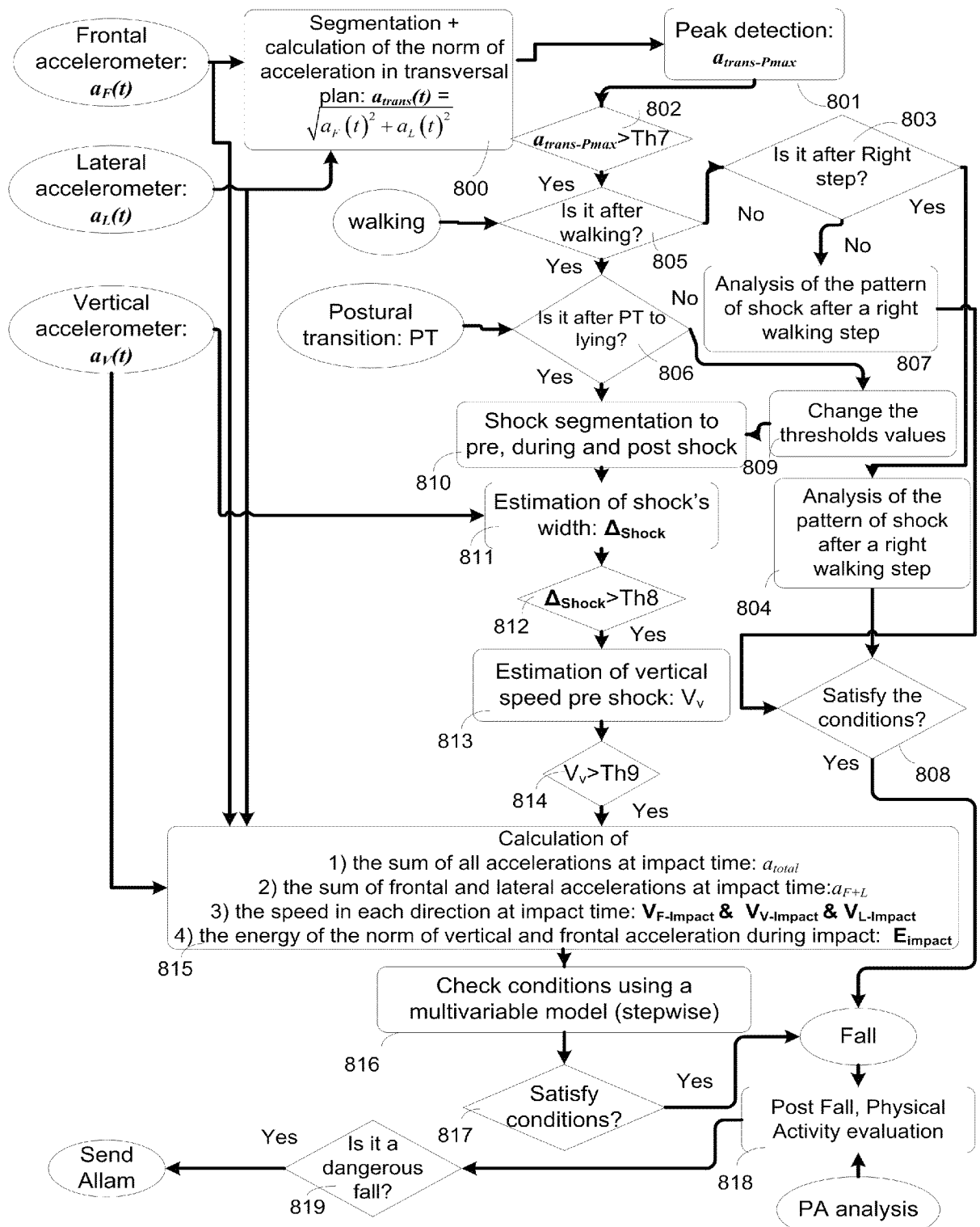
FIG. 8 is a flowchart of the algorithm used to automatically detect the subject's falls.

9) identify a fall event through a multivariable model (stepwise or linear combination) that uses the above descriptors as inputs and coefficients chosen in step (4) supra (box 816, FIG. 8);

10) identify a fall as "serious" if the post-fall activities represent an unusual activity pattern, such as a long-duration rest, or multiple unsuccessful postural transitions (boxes 818-819, FIG. 8); in one embodiment of the invention, an alarm will be set off following a "serious" fall;

II. Physical activity classification.

The algorithms described above will classify the subject's physical activity and posture, determine his or her risk of falling and quality of movements. In addition, several rules will be applied to improve the classifications performed by the above algorithms. These rules include, but are not limited to, the following:

1) If two contradictory states are detected (e.g., lying with walking or sitting with walking) preference is first given to lying, then to walking, and finally to postural transitions. This rule is based on the rationale that the lying posture is classified with the least amount of error. It should be noted that since the algorithms for different postural detections operate independently, two contradictory sets of activities may be identified.
2) Two successive postural transitions classified as the same type (e.g., SI-ST followed by SI-ST) are not possible—the classifications are modified according to the preceding and subsequent activities.
3) Elderly subjects cannot lean backwards after a SI-ST transition with a high likelihood. The algorithm estimates the trunk lean angle based on the trunk angle before ($\theta_{PT\text{-}pre}$) and/or following ($\theta_{PT\text{-}post}$) the postural transition.
   (i) Both $\theta_{PT\text{-}pre}$ and $\theta_{PT\text{-}post}$ are estimated based on the mean (E[.]) of the frontal acceleration during the rest period immediately before, or after a postural transition, according to the following formulas:

$\theta_{PT\text{-}pre} = \sin^{-1}(E[a_F(t)|\text{pre-}PT\text{-rest}])$ $\theta_{PT\text{-}post} = \sin^{-1}(E[a_F(t)|\text{post-}PT\text{-rest}])$ where $E[a_F(t)$ pre-PT-rest] denotes the mean of the frontal acceleration signal during the rest period immediately before the postural transition; $E[a_F(t)$ post-PT-rest] denotes the corresponding mean after the postural transition.
   (ii) If the standard deviation of both frontal and vertical accelerations during a local interval before or after a postural transition were lower than a pre-defined threshold, the algorithm will classify that duration as a rest period.
   (iii) Sensor inclination ($\theta_{initial}$) is computed from the average of the frontal accelerometer signal during a recognized walking episode containing at least ten steps: $\theta_{initial} = \sin^{-1}(E[a_F(t)\text{ walking; 10 steps}])$.
   (iv) The backwards-leaning state is detected if, subtracting $\theta_{initial}$ from $\theta_{PT\text{-}pre}$ (or $\theta_{PT\text{-}post}$) yields a value lower than a pre-defined threshold.
4) The duration of the lying posture should be more than a specified length (e.g., 30 seconds).
5) For an episode to be classified as "walking," it must include at least three successive steps within a pre-defined interval.
6) Since it is improbable for a person, especially an elderly subject, to stand for long periods without any movements, long standing periods without additional activity (e.g., more than three minutes) are interpreted as sitting. This rule applies if the standard deviations of both the vertical and frontal accelerations are below pre-defined thresholds.

REFERENCES

[1] B. Najafi and K. Aminian, "Body movement monitoring system for elderly people, determines time and duration of postural transition (2000, European and US Patent)," EP1195139-A1 EP810920 05 Oct. 2000; US2004015103-A1 U.S. Pat. No. 398,462 04 Apr. 2003, 2000.

[2] B. Najafi, K. Aminian, F. Loew, Y. Blanc, and P. A. Robert, "Measurement of stand-sit and sit-stand transitions using a miniature gyroscope and its application in fall risk evaluation in the elderly," *Ieee Transactions on Biomedical Engineering*, vol. 49, pp. 843-851, 2002.

[3] B. Najafi, K. Aminian, A. Paraschiv-Ionescu, F. Loew, C. J. Bula, and P. Robert, "Ambulatory system for human motion analysis using a kinematic sensor: Monitoring of daily physical activity in the elderly," *Ieee Transactions on Biomedical Engineering*, vol. 50, pp. 711-723, 2003.

[4] R. W. Bohannon, A. W. Andrews, and M. W. Thomas, "Walking speed: reference values and correlates for older adults," *J Orthop Sports Phys Ther*, vol. 24, pp. 86-90, 1996.

[5] K. Aminian, B. Najafi, C. Bula, P. F. Leyvraz, and P. Robert, "Spatio-temporal parameters of gait measured by an ambulatory system using miniature gyroscopes," *Journal of Biomechanics*, vol. 35, pp. 689-699, 2002.

[6] K. Aminian, B. Najafi, J. Gramiger, P. Morel, and N. Bijan, "Autonomous measuring unit for human movement has sensors, conditioning circuit, display, and circuit for recording kinematic parameters of body segment," ECOLE POLYTECHNIQUE FEDERALE LAUSANNE (ECOL-Non-standard) AMINIAN K (AMIN-Individual) BIJAN N (BIJA-Individual) GRAMIGER J (GRAM-Individual) MOREL P (MORE-Individual).

[7] K. Aminian, K. Rezakhanlou, E. De Andres, C. Fritsch, P. F. Leyvraz, and P. Robert, "Temporal feature estimation during walking using miniature accelerometers: an analysis of gait improvement after hip arthroplasty," *Medical & Biological Engineering & Computing*, vol. 37, pp. 686-691, 1999.

[8] S. R. Cummings, M. C. Nevitt, and S. Kidd, "Forgetting falls. The limited accuracy of recall of falls in the elderly," *J Am Geriatr Soc*, vol. 36, pp. 613-6, 1988.

[9] D. Oliver, M. Britton, P. Seed, F. C. Martin, and A. H. Hopper, "Development and evaluation of evidence based risk assessment tool (STRATIFY) to predict which elderly inpatients will fall: case-control and cohort studies," *Bmj*, vol. 315, pp. 1049-53, 1997.

[10] M. E. Tinetti, T. F. Williams, and R. Mayewski, "Fall risk index for elderly patients based on number of chronic disabilities," *Am J Med*, vol. 80, pp. 429-34, 1986.

[11] K. Doughty, R. Lewis, and A. McIntosh, "The design of a practical and reliable fall detector for community and institutional telecare," *J Telemed Telecare*, vol. 6 Suppl 1, pp. S150-4, 2000.

[12] U. Lindemann, A. Hock, M. Stuber, W. Keck, and C. Becker, "Evaluation of a fall detector based on accelerometers: a pilot study," *Med Biol Eng Comput, vol.* 43, pp. 548-51, 2005.

[13] Y. Depeursinge, J. Krauss, and M. El-Khoury, "Device for monitoring the activity of a person and/or detecting a fall, US Pat. No. 6,201,476," 2001.

[14] N. Noury, G. Barralon, G. Virone, P. Boissy, M. Hamel, and P. Rumeau, "A smart sensor based on rules and its evaluation in daily routines," presented at 25th Annual International Conference of the IEEE Eng. Med. Biol. Society, 2003.

What is claimed is:

1. A body movement monitoring system comprising:
   a sensor, adapted to be attached to an upper part of a body of a person, the sensor comprising an accelerometer component adapted to generate signals in response to movement of the body, the signals comprising a frontal acceleration signal and a vertical acceleration signal;
   one or more processor circuits programmed to:
   filter at least a portion of the signals generated by the accelerometer component to obtain a first set of filtered signals;
   determine an initial estimated postural transition duration for a first postural transition based on one or more peaks in the first set of filtered signals, and for a first time window;
   apply one or more additional filters to a segment of the signals generated by the accelerometer component to obtain a second set of filtered signals, the segment corresponding to only a second time window that is narrower than the first time window and that is selected based at least in part on a timing corresponding to the initial estimated postural transition duration for the first postural transition;
   determine a revised estimated postural transition duration that is more accurate than the initial estimated postural transition duration for the first postural transition based on a location of one or more peaks in the second set of filtered signals; and
   derive information related to the first postural transition using the revised estimated postural transition duration and the second set of filtered signals, the information including identification of at least one of a time of occurrence, a duration, and a type of the first postural transition.

2. The system of claim 1, wherein said one or more processor circuits are further programmed to:
   filter the frontal accelerometer signal of the signals from the accelerometer component with at least one time frequency filter to obtain the first set of filtered signals.

3. The system of claim 2, wherein said one or more additional filters applied to the first set of filtered signals comprises a multi-stage wavelet.

4. The system of claim 3, wherein said one or more processor circuits are further programmed to derive the information by at least:
   estimating an inertial acceleration of the person during a time period corresponding to the revised estimated postural transition duration, the estimating further comprising at least one of:
      processing the second set of filtered signals to correct for a sagittal trunk tilt angle of the person relative to the sensor during the time period corresponding to the revised estimated postural transition duration;
      applying one or more filters to the vertical acceleration signal from the time period corresponding to the revised estimated postural transition duration to obtain a third set of filter signals; and
      identifying one or more peaks in the third set of filter signals.

5. The system of claim 4, wherein the first postural transition is classified based on a positive extrema and a negative extrema of the one or more identified peaks in the third set of filter signals.

6. The system of claim 5, wherein the first postural transition is classified as:
a postural transition to standing when positive extrema of the vertical acceleration is followed by the negative extrema, and
a postural transition to sitting when negative extrema of the vertical acceleration is followed by the positive extrema.

7. The system of claim 1, wherein said one or more processor circuits are further programmed to:
identify a potential time period corresponding to a duration of walking of the person from the vertical acceleration signal by removing from consideration a portion of the vertical acceleration signal that is from a time corresponding to the first postural transition, the time based at least in part on the derived information; and
identify, in the potential time period, at least three peaks within a predefined time interval as an indicator of a walking pattern.

8. The system of claim 7, wherein said one or more processor circuits are further programmed to:
remove a portion of the signals attributable to the person's trunk oscillations for better identification of the walking pattern.

9. The system of claim 1, wherein the accelerometer component comprises a tri-axial accelerometer.

10. The system of claim 1, wherein the accelerometer component comprises a plurality of mono-axial accelerometers measuring accelerations in a plurality of perpendicular directions.

11. The system of claim 1, further comprising:
one or more data storage systems configured to store at least one of:
signals recorded by said sensor, and
the information derived by said one or more processor circuits.

12. The system of claim 1, further comprising:
a communications system configured to transmit data to a receiving system, the data comprising at least one of:
data reflecting at least a portion of the signals from said accelerometer component; and
at least a portion of the information derived by said at least one processor circuits.

13. A fall detection monitoring system comprising:
a sensor adapted to be attached to an upper part of a body of a person, the sensor comprising a movement detection component adapted to generate signals in response to a movement of the body; and
one or more processor circuits programmed to:
identify one or more peaks in the signals from the movement detection component; and
for at least one of the one or more identified peaks,
process the signals identify a non-fall activity performed by the person in a time period prior to a time period corresponding to the peak;
in response to identifying that the non-fall activity preceding the peak was a first type of non-fall activity, set one or more fall thresholds to a first set of one or more values;
in response to identifying that the non-fall activity preceding the peak was a second type of non-fall activity, set the one or more fall thresholds to a second set of one or more values; and
identify the peak as indicative of a fall event if the peak meets the one or more fall thresholds.

14. The system of claim 13, wherein the movement detection component comprises an accelerometer component.

15. The system of claim 14, wherein the signals comprise a frontal acceleration signal, a vertical acceleration signal, and a lateral acceleration signal, and wherein the one or more processor circuits are further programmed to identify one or more peaks in the signals from the movement detection component by:
determining a magnitude of acceleration in a traversal plane based on the frontal acceleration and lateral acceleration signals; and
detecting one or more peaks within the determined magnitude of acceleration in the traversal plane.

16. The system of claim 13, wherein said first type of non-fall activity comprises walking and said first set of one or more values are associated with either walking on a right step or with walking on a left step.

17. The system of claim 13, wherein said one or more processor circuits are further programmed to:
determine information related to physical activity of the person after a time period corresponding to the fall event; and
classify the fall event as a serious fall event if the determined information indicates that the fall event is followed by a long period of rest or multiple unsuccessful postural transitions in succession.

18. The system of claim 13, wherein said one or more processor circuits are further programmed to:
when the identified non-fall activity is not walking, segment a shock pattern identified based on the one or more peaks;
estimate a width of the shock pattern; and estimate a vertical speed of the person in a time period prior to a time period corresponding to the shock pattern.

19. The system of claim 13, wherein said one or more processor circuits are further programmed to:
record a history of one or more identified fall events; and
evaluate a risk of falling of the person based on:
the history of the one or more identified fall events within a pre-determined time period and one or more of:
a duration of postural transitions of the person within the pre-determined time period,
a number of identified postural transitions within the pre-determined time period,
a walking performance within the pre-determined time period, and
a longest detected duration of walking within the pre-determined time period.

20. The system of claim 19, wherein the pre-determined time period is a day.

21. A method of monitoring body movement using signals from a sensor adapted to be attached to an upper part of a body of a person, the sensor comprising an accelerometer component adapted to generate signals in response to movement of the body, the signals comprising a frontal acceleration signal and a vertical acceleration signal, the method comprising:
filtering, by one or more processor circuits, at least a portion of the signals generated by the accelerometer component to obtain a first set of filtered signals;
determining, by said one or more processor circuits, an initial estimated postural transition duration for a first postural transition based on one or more peaks in the first set of filtered signals and for a first time window;
applying, by said one or more processor circuits, one or more additional filters to a segment of the signals generated by the accelerometer component to obtain a second set of filtered signals, the segment corresponding to only a second time window that is narrower than the first time window and that is selected based at least in part on a timing corresponding to the initial estimated postural transition duration for the first postural transition;

determining, by said one or more processor circuits, a revised estimated postural transition duration that is more accurate than the initial estimated postural transition duration for the first postural transition based on a location of one or more peaks in the second set of filtered signals; and deriving, by said one or more processor circuits, information related to the first postural transition using the revised estimated postural transition duration and the second set of filtered signals, the information including identification of at least one of a time of occurrence, a duration, and a type of the first postural transition.

22. A method of detecting fall events using signals from a sensor adapted to be attached to an upper part of a body of a person, the sensor comprising a movement detection component adapted to generate signals in response to a movement of the body, the method comprising:

identifying, by one or more processor circuits, one or more peaks in the signals generated by the movement detection component; and for at least one of the one or more identified peaks,
  processing the signals to identify a non-fall activity performed by the person in a time period prior to a time period corresponding to the peak;
  if the non-fall activity preceding the peak was identified as a first type of non-fall activity, setting one or more fall thresholds to a first set of one or more values;
  if the non-fall activity preceding the peak was identified as a second type of non-fall activity, setting the one or more fall thresholds to a second set of one or more values; and
  identifying the peak as indicative of a fall event if the peak meets the one or more fall thresholds.

* * * * *

UNITED STATES PATENT AND TRADEMARK OFFICE
CERTIFICATE OF CORRECTION

PATENT NO. : 8,206,325 B1
APPLICATION NO. : 12/249948
DATED : June 26, 2012
INVENTOR(S) : Bijan Najafi et al.

It is certified that error appears in the above-identified patent and that said Letters Patent is hereby corrected as shown below:

In the Drawings:

In Sheet 2 of 8 (Reference Numeral 210 Fig. 2), change "sagital" to -- sagittal --.

In Sheet 7 of 8 (Reference Numeral 703 Fig. 7), change "succesive" to -- successive --.

In the Specifications:

In Column 6, Line 51, change "Thl;" to -- $Th_1$; --.

In Column 7, Lines 46-50 (Approx.),

Change "
$$\begin{bmatrix} a_{F-inertial}(t) \\ a_{V-inertial}(t) \end{bmatrix} = \begin{bmatrix} \cos(\theta(t)) & -\sin(\theta(t)) \\ \sin(\theta(t)) & \cos(\theta(t)) \end{bmatrix} \begin{bmatrix} a_F(t) \\ a_V(t) \end{bmatrix} + \begin{bmatrix} 0 \\ 1 \end{bmatrix},$$
"

to --
$$\begin{bmatrix} a_{F-inertial}(t) \\ a_{V-inertial}(t) \end{bmatrix} = \begin{bmatrix} \cos(\theta(t)) & -\sin(\theta(t)) \\ \sin(\theta(t)) & \cos(\theta(t)) \end{bmatrix} \begin{bmatrix} a_F(t) \\ a_V(t) \end{bmatrix} - \begin{bmatrix} 0 \\ 1 \end{bmatrix};$$
--.

In Column 8, Line 60, change "$a_{V\text{-}filt}(t)$" to -- $a_{V\text{-}filt3}(t)$ --.

In Column 8, Line 62, change "$a_{V\text{-}filt}(t)$" to -- $a_{V\text{-}filt4}(t)$ --.

In Column 11, Line 25, change "lying." to -- lying; --.

Signed and Sealed this
First Day of October, 2013

Teresa Stanek Rea
*Deputy Director of the United States Patent and Trademark Office*

CERTIFICATE OF CORRECTION (continued)
U.S. Pat. No. 8,206,325 B1

In Column 11, Line 34 (Approx.), change "lying." to -- lying; --.

In the Claims:

In Column 15, Line 53, In Claim 13 after "signals" insert -- to --.